United States Patent [19]
Blauch et al.

[11] Patent Number: 5,265,462
[45] Date of Patent: Nov. 30, 1993

[54] METHOD AND APPARATUS FOR DETERMINING PERMEABILITY, DIFFUSIVITY, POROSITY, AND GAS STORAGE IN GAS-CONTAINING SUBSTRATES

[75] Inventors: Matthew E. Blauch, Duncan; Milton B. Enderlin, Bartlesville; Hazim H. Abass, Duncan; David E. McMechan, Marlow, all of Okla.

[73] Assignee: Halliburton Company, Duncan, Okla.

[21] Appl. No.: 882,195

[22] Filed: May 13, 1992

[51] Int. Cl.$^5$ .................................. G01N 15/08
[52] U.S. Cl. .................................................. 73/38
[58] Field of Search ............ 73/38, 153, 19.01, 19.04, 73/19.05

[56] References Cited

U.S. PATENT DOCUMENTS

| | | | |
|---|---|---|---|
| 3,114,256 | 12/1963 | Palmer | 73/38 |
| 3,839,899 | 10/1974 | McMillen | 73/38 |
| 4,555,934 | 12/1985 | Freeman et al. | 73/38 |
| 4,573,342 | 3/1986 | Jones | 73/38 |
| 4,627,270 | 12/1986 | Jones | 73/38 |
| 4,817,423 | 4/1989 | Christiansen | 73/153 |
| 4,864,845 | 9/1989 | Chandler et al. | 73/38 |
| 5,109,716 | 5/1992 | Ito et al. | 73/38 |

FOREIGN PATENT DOCUMENTS 262348 11/1988 German Democratic Rep. .
649-989 2/1979 U.S.S.R. .

OTHER PUBLICATIONS

Petroleum and Natural Gas Section of the Proceedings of the Third Pennsylvania Mineral Industries Conference, State College, Pa., pp. 113-117, 1933.
SPE Formulation Evaluation, Feb. 1986 Article entitled "Dynamic Gas Slippage: a Unique Dual-Mechanism Approach to the Flow of Gas in Tight Formations" by Ertekin et al.—pp. 43-52.

Primary Examiner—Hezron E. Williams
Assistant Examiner—Michael Brock
Attorney, Agent, or Firm—Robert A. Kent; Bradley M. Ganz

[57] ABSTRACT

The permeability and/or porosity of gas-containing substrates, particularly substrates of low permeability, can be determined by sealing a gas-containing substrate in a sealable "core analysis vessel" of known or ascertainable volume as soon as possible after removing the sample from the subsurface. Because the sealed sample is still at about formation pressure, gas will leak from the sample into the space of the vessel. The pressure build-up over time in the core analysis vessel is measured. When the pressure has equilibrated, the pressure is vented through a flowmeter to determine gas volume, followed by venting to atmosphere. The system is resealed and then the process is repeated until no subsequent pressure build-up occurs. By knowing the internal volume of the chamber, the bulk volume of the core sample, and recording the pressure build-up as a function of the time, many substrate properties, such as pore volume and permeability, can be calculated via standard methods. The effective pore volume which the gas originally occupied can be directly measured by venting the gas in the core analysis vessel to the external pressure through a flow-volume measuring device.

6 Claims, 4 Drawing Sheets

FIG. 3

METHOD AND APPARATUS FOR DETERMINING PERMEABILITY, DIFFUSIVITY, POROSITY, AND GAS STORAGE IN GAS-CONTAINING SUBSTRATES

BACKGROUND OF THE INVENTION

1. Field of the Invention

This invention relates to a method and apparatus for determining the permeability and/or porosity of a gas-containing substrate.

2. Description of the Related Art

Subsurface deposits of gas and oil are generally trapped in porous rock under greater than atmospheric pressure. Formation rocks have widely varying permeability and porosity and are generally categorized as sandstones, shales, and carbonates. The permeability of any given hydrocarbon-bearing formation correlates with how fast gas and/or oil may flow through the formation. The porosity of the formation correlates with the volume of gas or oil the formation may hold. Thus, an understanding of a formation's permeability and porosity is important for formulating well completion and production strategies for the formation. Various methods have been used for estimating permeability and porosity. Unfortunately, each method has its disadvantages; a common disadvantage concerns imprecision and difficulty in dealing with low permeability and porosity formations.

An instrument known as a core-permeameter has been used for non-destructive measurement of rock permeability. For a description of such a device see Chandler et al., U.S. Pat. No. 4,864,845. A permeameter is generally constructed of a narrow elastomer tube connected to a compressed gas source. The elastomer is pressed with a controlled force against the cylindrical, clean rock surface. A gas under a known pressure is forced from one end of the tube through the rock's pores. A flow meter measures the gas flow rate. The permeability of the sample is calculated from the flow rate and the applied pressure. The gas flow rate is estimated by a series of flow meters or orifice tubes which are selected to accurately cover a wide range of possible rates. An estimate of the permeability may be obtained by calibrating the mini-permeameter flow rate for various core plug samples of known permeability. On-site field operation of permeameters, however, has been a laborious task prone to frequent error. Thus, to obtain the permeability of a rock formation in situ using a permeameter, measurements are made at multiple sites at spaced intervals in an array or grid. Although the sensing of permeability occurs rapidly at each test site, the overall process requires a considerably greater amount of time for leveling the instrumentation, monitoring the flow rate, adjusting pressure, and recording the field measurements. Also, a bulky cylinder or an air compressor is generally needed to supply the relatively large amount of air required for multi-site testings.

In situ measurements of rock formations have also been made by a well test method, which involves monitoring changes in the pressure of a borehole as fluid is pumped out. One disadvantage of this technique is that only an average permeability is obtained; details on the permeability of heterogenous structures within the formation remain undefined. Furthermore, actual well production often does not correspond to forecasts.

Another commonly used method has involved extracting a core plug from the formation. The plug is then placed in a rubber sleeve known as a Hassler sleeve, and is sealed in place by a confining pressure applied to the outside of the sleeve. A pressure difference is applied across the length of the plug to induce flow through the plug. The rate of flow and a pressure difference are measured. Permeability is then computed by a mathematical formula known as Darcy's law. This approach is described, for example, in Freemann et al., U.S. Pat. No. 4,555,934 and Jones et al., U.S. Pat. No. 4,573,342. Although this approach allows for more detailed studies of formation permeability, it is very time consuming and sometimes not feasible, particularly on low permeability samples. Moreover, it does not measure permeability in situ, and it is destructive to samples. Furthermore, a porosity determination requires separate testing.

An x-ray CT or CAT scan imaging technique using xenon gas has also been suggested generally for determining porosity distribution in a whole core sample. This imaging technique has not been useful for determining permeability and required the use of a CT scanner facility.

Conventional preparation and measurement techniques are known to yield inaccurate estimates of a formation's permeability and porosity. For instance, core preparation techniques can alter a core sample and critically affect the ultimate determination of its permeability and porosity. For example, prepared cores often are exposed, dried, and treated with solvents. Further, some conventional core study techniques use a plug that is drilled from a standard whole core sample. During the drilling process, liquid nitrogen or other fluid may be applied to the core sample, and thereby alter the intrinsic nature of the sample. Consequently, core measurements made under current techniques all too often do not accurately portray a formation's native permeability or porosity due to sample alteration.

In general, conventional techniques lack the sensitivity to measure very low permeability formations. These techniques are mainly suitable for formations whose permeability ranges from millidarcies to darcies, such as sandstones. Shale, however, is a much tighter formation rock, whose permeability typically is in the microdarcies to nanodarcies range.

In addition to the above inaccuracies, other drawbacks exist in conventional methods. For example, it is very difficult, if not impossible, to concurrently measure porosity (gas storage volume), diffusivity and permeability using conventional methods. Moreover, many of the currently known techniques, particularly those used to test shales, destroy the samples, leaving nothing for use in further types of testing.

SUMMARY OF THE INVENTION

The present invention addresses one or more of the above-mentioned drawbacks in the prior art. Thus, the invention in a general aspect provides a device and method for more accurately estimating the permeability and/or porosity of gas-containing substrates, particularly substrates of low permeability. The invention does this without forced flow of gas or fluid through the core. Basically, the invention measures the pressure build-up and gas volume in a sealed chamber containing a recently extracted core sample still virtually in its subsurface state. This invention also reduces or eliminates the need for traditional core preparation and the concomitant possibility of core alterations. The present invention further provides a system of analysis which does not destroy or alter the sample, thereby preserving the sample for further types of testing. The device and methods described herein are also capable of concurrently determining other qualities of the sample, such as gas composition, gas storage volume and diffusivity.

One general embodiment of the invention comprises a sealable core analysis vessel of known or ascertainable volume for holding a substrate having a known or ascertainable volume, the vessel having at least one outlet port and at least one instrumentation assembly for venting gas in the vessel through the outlet port to instrumentation. For purposes of this invention, "instrumentation assembly" comprises the means used to make connections between the core analysis vessel and instrumentation, so that gas can be vented through an outlet port of the core analysis vessel to, for example, particular kinds of instrumentation, a gas expansion chamber(s), or to atmosphere.

The instrumentation preferably includes a suitable device for measuring how pressure in the vessel changes with time, such as a pressure transducer or analog gauge. Also preferably included is a meter for measuring gas flow and volume, as well as a device for measuring the temperature within the vessel, such as a thermocouple. Still other instrumentation may be employed, such as a gas analyzer, or transducers or other detectors for detecting strain or changes in the substrate's shape as gas diffuses from the substrate into the core analysis vessel. A gas expansion chamber may also be involved in collecting gas vented from the core analysis vessel, or venting gas to the atmosphere or other collection vessel. A data acquisition system for recording and processing data, such as a computer or analog equipment, can be connected to the instrumentation. In general, the ratio of the volume of the core analysis vessel to the bulk volume of the sample should be about 1.1 to 1.5.

In a variation of the above-described embodiment, a down-hole pressure containment vessel may serve as the vessel for holding the substrate. Again, this vessel should have at least one outlet port, and at least one instrumentation assembly, wherein gas in the vessel may be vented through the outlet port to the instrumentation. The instrumentation typically can be the same as that described in the previously described embodiment.

In another embodiment, the present invention comprises a method for determining the permeability and/or porosity or gas storage volume of a gas-containing substrate. A sample of the substrate is placed inside a core analysis vessel of known or ascertainable volume as soon as possible after the sample has been extracted from below the surface. Next, the system is sealed and sufficient time is allowed for the gas in the sample to diffuse out of the sample into the space of the core analysis vessel. As the gas diffuses, the resulting pressure build-up in the vessel is measured over time. During the monitoring of the pressure, the temperature is also preferably monitored.

When the pressure in the vessel has equilibrated, the gas inside the vessel can be vented through a flow/volume measuring device to an expansion chamber where the gas may be collected, or through the expansion chamber to the atmosphere. Flow/volume measurements can also be taken as gas is vented through the gas expansion chamber to the atmosphere. Venting involves releasing the gas in the core analysis vessel to a lower external pressure, generally the ambient pressure.

After gas in the core analysis vessel has been vented, the core analysis vessel is resealed. The equilibration, venting and resealing process is then repeated until the pressure of gas contained in the substrate equilibrates to about that in the gas expansion chamber. The bulk volume of the sample is also preferably determined. In general, the ratio of the volume of the core analysis vessel to the bulk volume of the sample should be about 1.1 to 1.5. Based on the various measurements, the sample's permeability and/or porosity may be calculated from combinations of some or all of the following: the vessel's volume; the sample's bulk volume; the measurement of pressure change in the vessel over time; the measurement flow/volume; and the measurement of the core analysis vessel's temperature at which the readings were taken.

This method may be varied, as for example, by providing for a down-hole sealing of the sample directly in the core analysis vessel. After down-hole containment, the core analysis vessel is then brought to the surface and vented to the external pressure chamber. After venting, the vessel is resealed. The sample is then allowed to equilibrate, with measurements taken according to the above-described steps. The invention can also be "reversed" wherein a gas depleted substrate is first placed in the core analysis vessel, the vessel is repressurized to approximate the pressure native to the sample (i.e., the pressure a sample is subject to in its subsurface state), and kept at that pressure for sufficient time for the substrate to internally equilibrate to that pressure. Upon equilibration, the core analysis vessel is vented to ambient pressure and sealed. Following this, the invention is carried out in accordance with the same steps used for a non-depleted substrate, as previously described.

While the inventions described herein are contemplated to be useful on gas-containing substrates that vary widely in permeabilities and porosities, they are particularly useful on low permeability substrates, such as, for example, shales, tight sandstones, and tight carbonates.

DETAILED DESCRIPTION OF THE PREFERRED EMBODIMENTS

Figure 1:
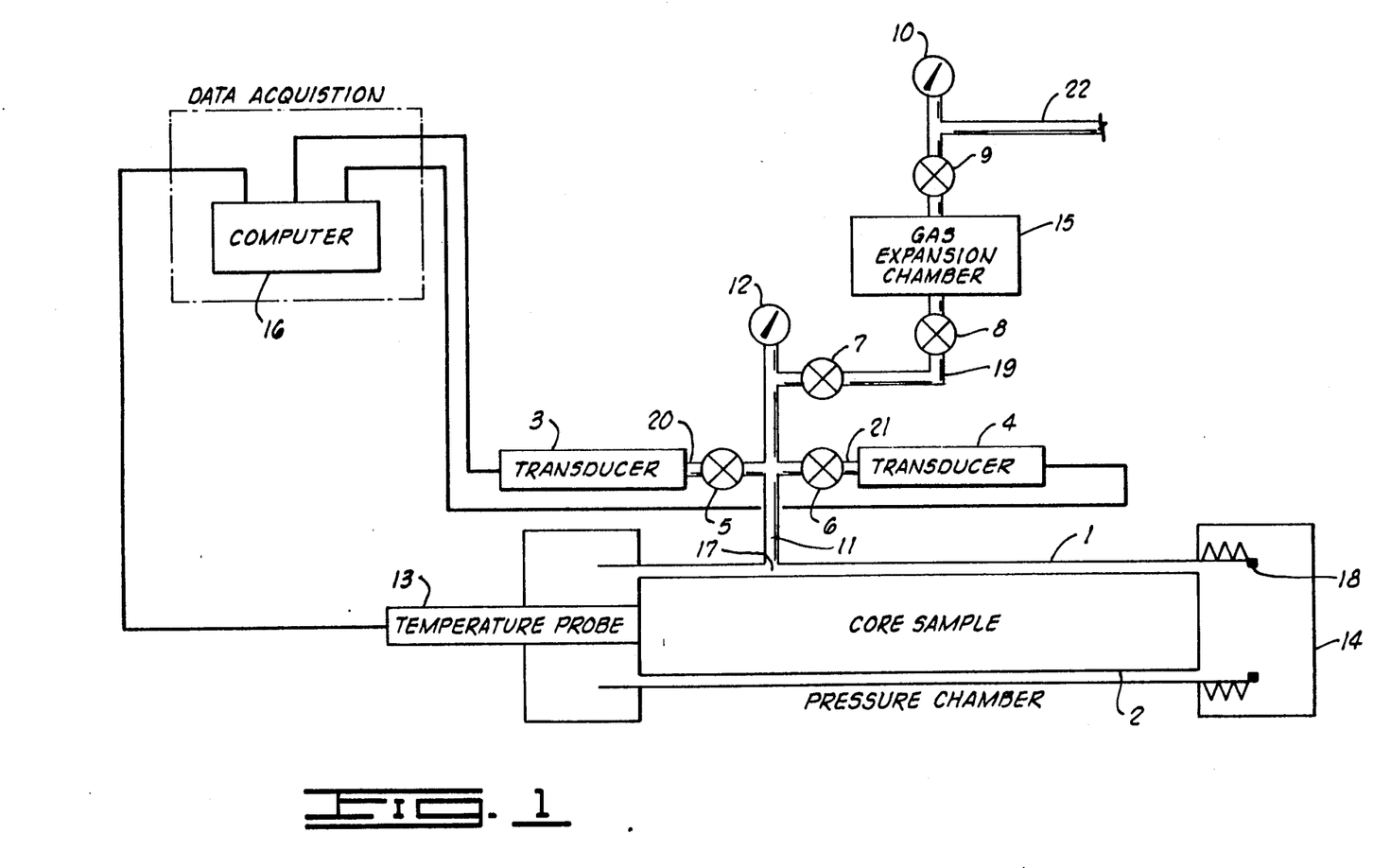
FIG. 1 depicts an exemplary test facility in accordance with the present invention, illustrated in schematic view.

The present invention comprises a highly sensitive device for accurately estimating, among other things, the permeability and porosity of a gas-containing substrate, particularly that of a substrate as it exists at or near reservoir conditions. FIG. 1 represents one of many possible embodiments of the present invention. It will be appreciated by persons of ordinary skill in the art to which this invention pertains that numerous equivalent devices and methods may be employed to achieve the same or similar results as the embodiment shown in FIG. 1, and the embodiments discussed herein.

FIG. 1 is illustrative of one of many possible embodiments of the present invention. This figure shows a core analysis vessel 1 in which a sample 2 can be placed; pressure transducers 3, 4; a flow/volume measuring device 10; control valves 5, 6; a utility gauge, for e.g., instantaneous pressure readings or flow/volume measurements 12; flow/volume control valves 7, 8, 9; pressure tubing 11, 19, 20, 21, 22; a pressure cap 14; a gas expansion chamber 15; an outlet port 17; a temperature probe 13; a data acquisition system, such as a computer with appropriate software, 16 which can be interfaced With instrumentation, e.g., 3 and 4 and an O-ring pressure seal 18.

Before providing a brief summary of the general operation of the invention, it is first noted that when a core sample of low permeability rock is taken from the subsurface and exposed to atmospheric conditions, gas trapped in the core slowly leaks out. The permeability and porosity of a sample are determined based on the propensity of a sample to leak gas. Thus, a sample is sealed in a core analysis vessel upon or as soon as is practicable after exposure to atmospheric pressure or other pressure less than formation pressure. It is considered that exposures of less than several hours to surface pressures less than formation pressure will not appreciably affect measurements of permeability and porosity. As the gas leaks out of the core sample 2, the pressure in the core analysis vessel 1 starts to build-up with valve 7 being closed and valves 5 & 6 being open. If the core sample 2 is believed to have a high permeability, then to prevent excess gas leakage before sealing the sample in the core analysis vessel, down-hole pressure containment of the sample is recommended, as described below. By recording the pressure build-up as a function of time, and knowing both the internal volume of the vessel and the bulk volume of the core sample, many rock properties such as pore volume gas storage, diffusivity, and permeability may be calculated by mathematical formulas discussed herein. Additionally, porosity may be directly determined by venting through the flow/volume measuring device 10. A more thorough description of the invention follows.

Before use, the test apparatus is purged with nitrogen or any other suitable gas. A standard core sample 2 may be subjected to down-hole pressure containment in the container that will serve as the core analysis vessel 1 to which instrumentation is connected. Alternatively, the core sample 2 may be brought to the surface and placed in a suitable core analysis vessel, to which instrumentation is then connected. If the core is not subjected to down-hole pressure containment, it is placed into the core analysis vessel 1 as soon as the core sample 2 has been retrieved from the subsurface. The size of the vessel 1 may vary depending on the length and diameter of the core sample 2 to be tested. In that regard, the present invention preferably uses a surface containment core analysis vessel 1 large enough to hold a core sample 2 four inches in diameter and three to five feet long. These dimensions, however, can be changed to meet particular needs. The core analysis vessel 1 can be constructed from, for example, a cylinder closed at one end and sealed with a pressure tight cap 14 at the other. In constructing a core analysis vessel 1, the dead space remaining in the vessel after placement of the sample should be minimized. In general, the ratio of the volume of the core analysis vessel to the volume of the sample should be about 1.1 to 1.5. However, the tolerance of dead space ultimately is a function of instrumentation sensitivity: as instrumentation sensitivity increases, so can the amount of tolerable dead space. In that vein, it should be noted that the larger the sample, the more representative it will generally be of the formation.

If it is desired to minimize pre-containment gas leakage, the sample's bulk volume, if needed, may be determined after analyzing the sample in the device.

Although it is not expected that any significant pressure leakage from the sample would result from first extracting a core sample from the subsurface and then placing it into a core analysis vessel 1 at the surface, a subsurface placement in the core analysis vessel 1 could eliminate any leakage or pressure loss that might occur at the surface.

Devices are known whereby a core can be sealed into a vessel subsurface at formation pressure. For example, Eastman Christensen of Salt Lake City, Utah, a Baker-Hughes Co., manufactures and sells such a containment vessel (or "core barrel") for a whole core. The containment vessel itself may be adapted to serve as the core analysis vessel used in taking measurements of permeability and porosity. A valve or seal can be built into the vessel for coupling with instrumentation. Once brought to the surface, the containment vessel/core analysis vessel is vented to an external pressure chamber, and sealed again. Pressure build-up measurements and other measurements may then proceed.

Both subsurface and surface core analysis vessels 1 may be constructed from any standard pressure resistant material capable of withstanding formation pressures. Normally accepted safety parameters for the expected pressures should be taken into consideration. The vessel should also be resistant to any corrosive gases found in formations, such as hydrogen sulfide. Further, the vessel must be compatible with the necessary pressure connections (e.g., 5, 6, 11, 19, 20, 21 & 22). Once a sample is placed in the core analysis vessel and the vessel is sealed by, for example, a pressure cap 14 with an O-ring pressure seal 17, the pressure in the core analysis vessel 1 will equilibrate to above external pressure because of gas leakage from the sample 2. The pressure build-up over time is measured either incrementally, or continuously, until equilibration occurs.

After the pressure build-up over time is measured, or if no pressure build-up measurement over time is desired, the effective pore volume originally occupied by the gas may be calculated directly by venting the core analysis vessel to a gas expansion chamber 15 through valves 7 and 8. The vented gas can pass through a flow/volume measuring device such as a wet test meter either before or after passing through, or being collected in, the gas expansion chamber 15. This step usually will be coordinated with the taking of one or more pressure build-up measurements.

Once the pressure is vented to an expansion chamber 15, the process is preferably repeated by once again sealing (e.g., closing valves 7 and 8) the system so that it equilibrates to above external pressure (generally the ambient pressure). During the course of the equilibration, pressure build-up over time is monitored. After each repetition the amount of trapped gas in the sample diminishes, and the sample should equilibrate to a lower pressure than the previous time. Repetition is no longer necessary when the core sample has fully equilibrated to an external pressure, which generally is the atmospheric pressure. Equilibration is complete when no subsequent pressure build-up occurs in the core analysis vessel 1. A profile of the equilibration can be useful in providing an understanding of reservoir quality—e.g., the producibility of a well.

Each equilibration may require about two weeks or more. The amount of time required to analyze any particular core sample is a function of a rock's intrinsic properties. Some types of rock will equilibrate faster than others. For any particular sample, the number of required repetitions is a function of the amount of dead space remaining in the core analysis vessel 1 after the sample 2 has been placed inside. Dead space may be varied by changing vessel or sample size. By decreasing the dead space, more repetitions will be required; the more repetitions, the more accurate the information.

The instrumentation (e.g., 3, 4, 10, 12, 13) connected to the core analysis vessel 1 generally is standard equipment, readily available or known to those skilled in the art. The instrumentation need not be permanently connected to the core analysis vessel, but can be detachable. If instrumentation is not connected to a core analysis vessel when a sample is placed in it, any unmonitored pre-connection pressure build-up is expected to be insignificant if the connections are made within several hours. However, even if much time has passed before instrumentation is connected, it is expected that it will usually be possible to extrapolate back to the time the sample was placed in the vessel.

The invention's most basic required instrumentation from which permeability and porosity can be measured is pressure measuring instrumentation 3, 4, 12. Other desirable instrumentation includes, but is not limited to, a flow/volume measuring device 10 or 12 capable of measuring cumulative volume over time (preferred) and/or incremental rate. Example devices include a wet test meter or fluid-filled graduated cylinder and a temperature measuring device 13. Further contemplated instrumentation includes a device for detecting changes in sample strain or shape; and a device for analyzing a sample's gas composition.

Instrumentation should be as sensitive as possible in view of the invention's aim of determining the permeability of low permeability substrates. Generally, this means electronic instrumentation should be used. Measurements from the various instruments can be taken incrementally, or, preferably, continuously. It is also preferred that the instrumentation be interfaceable with a computer, (e.g., 16).

The pressure measuring device 3, 4, 12 may be selected from numerous commonly available devices. A highly sensitive pressure transducer capable of measuring to at least one hundredth of a pound per square inch, is preferred.

The flow/volume measurement may be by any of several available techniques, including by flow meter 10, 12, wet-test meter or through displacement in an inverted graduated cylinder filled with water.

For temperature measurement, a thermocouple 13 can be inserted into the dead space of the vessel and fitted with standard electrical and pressure fittings. A device that can continuously monitor temperature is preferred. Alternatively, the invention may be performed in a controlled temperature environment.

To detect any structural changes in the core sample, such as strain relaxation, and shape, an acoustic device may be connected within the vessel. Changes in strain and shape may also be detected by a differential linear displacement transducer. Or, one or more strain gauges may be used to monitor changes in the physical dimensions of the sample. For these devices, any standard electrical connections may be used.

Other useful information may be determined concurrently with measurements of permeability and porosity. For example, compositional gas analysis instrumentation may be used to determine the ratio of ethane and methane in the gas trapped in a core sample. That ratio can be an important indication of a well's potential production value and the composition used to determine Z factor.

The instrumentation may be connected to the core analysis vessel through standard pressure connections, tubings 11, 19, 20, 21 & 22, pipe-fittings and O-rings 18, bearing in mind that the connections should preferably be resistant to substances found in hydrocarbon formations, such as hydrogen sulfide. The instrumentation may connect to the vessel through one or more outlet ports 17. For example, one outlet port may vent to the pressure measuring device 3, 4, and a separate port may vent to a gas-flow meter. Still another possibility is venting a gas-composition analysis instrument. Alternatively, one outlet port could serve to vent to all instrumentation. An outlet port 17 can be mated with an instrumentation assembly for venting and connecting to the instrumentation.

As previously stated, an "instrumentation assembly" comprises the means used to make connections between the core analysis vessel and instrumentation, so that gas can be vented, for example, through an outlet port of the core analysis vessel to particular kinds of instrumentation and/or to a gas expansion chamber(s) 15 or to atmosphere. Accordingly, a valve 5, 6 and tubing, or associated components, such as O-rings, fittings, and the like are possible components of an instrumentation assembly (collectively, e.g., 5, 6, 11.) An instrumentation assembly may connect to one or more types of instruments. Detachability of instrumentation from control valves 5, 6, 7, 8, 9 is desirable for ease of substituting instrumentation on the core analysis vessel or transporting the vessel. In FIG. 1, valves 5, 6 & 7 are examples of control valves that may be located between an outlet port 17 and instrumentation 3, 4, 10, and 12. Another example of an instrumentation assembly might comprise 7, 8, 19, 15, 9, & 22.

Mathematical equations that may be used in the practice of the invention to calculate permeability and/or porosity are discussed in the following example.

EXAMPLE OF PROCEDURES

The following is one example of the many possible embodiments of this invention.

A 30 ft. long section of 4 inch diameter whole core was obtained from a "tight" gas bearing shale reservoir. The cored section was drilled using an air-mist fluid. The whole core was obtained with an aluminum "inner liner" core barrel by Eastman Christensen.

Approximately 1 hour of elapsed time was required to retrieve the core section from the subsurface. An additional 2 hours were required to cut the core sections including the aluminum liner and to select a suitable sample for placement into a core analysis vessel.

The core used in the experiment was a four foot section from 3,415 to 3,419 ft. below the surface. This section was first cleaned using a dry cloth and then placed into the chamber. The chamber was then sealed, the pressure monitoring equipment, thermocouple, and electronic cables were attached to a portable data acquisition system. The chamber was then thermally insulated and placed in a thermostatically controlled room. Ambient temperature ranged from 70 degrees F. to 75 degrees F. through the duration of the test.

Chamber pressure and temperature was monitored and recorded on floppy disk for a period of 12 days. A maximum of approximately 7 psi was measured. In this example, only one pressure equilibration was obtained. Volume expansion into the expansion chambers was not required due to the low initial pressure and sufficient dead-volume.

Figure 2:
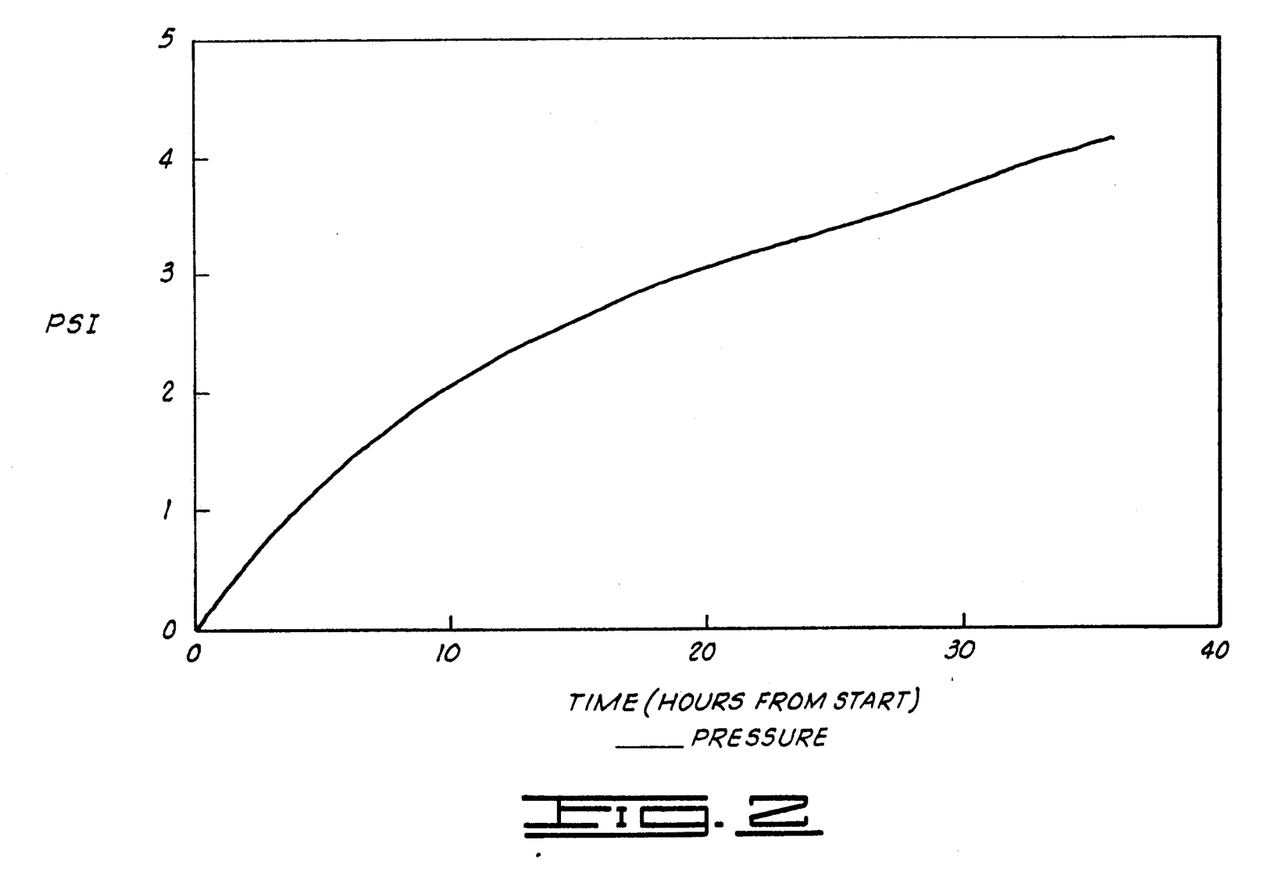
FIG. 2 depicts a curve showing the increase in pressure in the core analysis vessel from the time the sample is placed in the vessel over 40 hours.

The resultant pressure vs. time curve (FIG. 2) was generated from the recorded test data points.

Data was loaded into a LOTUS spreadsheet for data processing and generation of graphical output.

EXAMPLE CALCULATION

A simplified example calculation of sample core permeability is provided using the diffusivity equation proposed theoretically by Ertekin, et al. (*Dynamic Gas Slippage: A Unique Dual-Mechanism Approach to the Flow of Gas in Tight Formations*, SPE Formation Evaluation, February 1986.) These calculations were performed on a commercial PC based spreadsheet. The calculations can be refined to provide an improved theoretical model of the P vs. T response. For example, pressure was averaged across the entire core radius in one step for this example. The pressure profile across the core radius can be broken into a number of incremented segments to refine the calculations. More complex flow equations may also be used in a similar manner as the example calculation to account for the effects of bulk flow, diffusion, and desorption effects.

Figure 3:
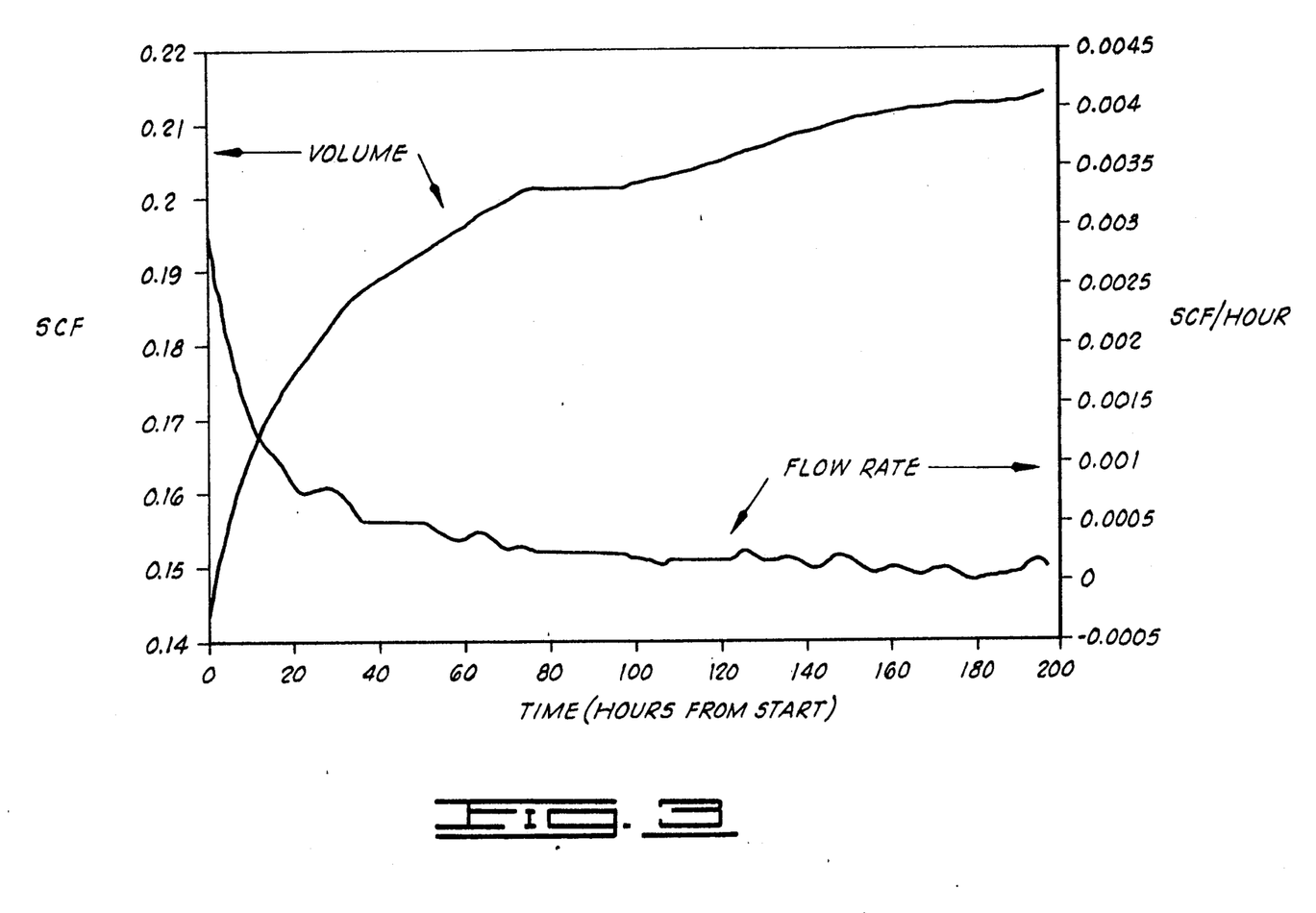
FIG. 3 depicts a curve representative of the conversion of pressure vs. time data to volume vs. time in terms of standard cubic feet (SCF) and flow rate (Q) vs. time in SCF/Hour units.

For the given pressure vs. time record (FIG. 2), pressure vs. time values are converted into rate vs. time using the following process.

a. Test Parameters
Chamber Length (ft)=4.5
Chamber Dia. ID (in)=4.5
Core Dia. OD (in)=4.0
Core Length (ft)=4.0
Chamber Volume (ft$^3$)=0.49201
Core Volume (ft$^3$)=0.344716
Annular Volume (ft$^3$)=0.152294 b. From Equation Nos. 1 and 2 (described below), the pressure vs. time data is converted to volume vs. time in SCF (Standard Cubic Feet) and Q (flow rate) vs. time in SCF/Hour units as shown in FIG. 3.

$$B_g = \frac{P_s Z T_r}{T_s P_r} = \frac{\text{gas volume @ } P_r}{\text{gas volume @ STP}} = \frac{\text{cuft}}{\text{SCF}} \quad \text{Equation 1}$$

Assume:

$P_s$ = 14.65 psi
$T_s$ = 520 °R
$T_r$ = °R (input from temp. recorder)
$P_r$ = psi (input from data)
$Z$ = Gas compressibility factor for given gas composition as $P$ (Assume a value of 1 in Example)
$B_g$ = Gas volume factor $\frac{\text{vol. in cuft @ reservoir conditions}}{\text{vol. in cuft @ STP conditions}}$

*Annular space gas volume is known or calculated for a given bulk volume of core using standard measuring techniques following the pressure recording measurements.

**In this example calculation, the annular volume is calculated to be 0.152294 ft$^3$ Pressure vs. time data can then be converted into rate vs. time performance for the given test. Assuming that gas flow is dominated by the diffusion process, Fick's law of diffusion is applied as follows:

$$\frac{Q}{A} = D \frac{dc}{dr} \quad \text{Equation 2}$$

where:

$Q$ = gas flow rate (lbm/day)
$A$ = flow area rate (ft$^2$) Surface Area of Core
$D$ = diffusivity coefficient (ft$^2$/day)
$\frac{dc}{dr}$ = gas concentration gradient To determine the gas concentration, $C_o$ inside the core, the cumulative gas produced through the test is calculated. This reflects $C_o$ at initial conditions.

Calculation of Produced Gas

The annular volume does not change during the test.

Initial conditions at the time the chamber is sealed provide the initial quantity (moles or SCF) of gas in the annulus. $P_1$, or initial pressure is atmospheric pressure. Initial temperature of the chamber is recorded by the data acquisition system. The initial quantity of gas is then calculated via the basic gas law:

$$P V = Z N R T$$

where:
P=equilibrated gas pressure
V=volume
Z=compressibility factor
N=quantity of gas in moles
R=universal gas constant
T=temperature At the conclusion of the test, the pressure(P), Z, and temperature can potentially change from initial conditions in addition to the gas quantity. To account for the re-equilibration, measured pressure and temperature with calculated Z are used to calculate a new gas quantity, $N_{final}$.

Then, $N_{final} - N_{initial}$ = cumulative gas produced.

If the assumption is made that the system has reached equilibrium (i.e., annulus pressure and internal core pressure are equal and constant) then the quantity of gas remaining in the core can be calculated if the pore volume is known. Produced gas plus remaining gas equals the original gas in the core (at the start of the test). This is used in the same equation to calculate the initial average pressure in the core, or $P_2$.

A core porosity value is independently determined, calculated, or assumed based on Boyle's Law helium porosimetry.

It should be noted that by adding or extracting a known quantity of gas after the system has reached equilibrium, and allowing it to reach a new equilibrium, the porosity of the core can be directly determined if the measured bulk volume (BV) is known. BV can be determined by knowing the core dimensions or through a variety of fluid displacement methods which are familiar to those skilled in the art.

However, if the permeability of the core is very low, (as in most cases with this device), an expansion chamber 15 of known volume can be connected to the core analysis vessel 1. The connected chamber is then filled with gas to a different pressure than the ore chamber. The connection between the chambers should be large enough to allow the pressure in the two chambers to reach equilibrium rapidly enough so that there is negligible flow into (or out of) the core before equilibrium is reached when the valve between the chamber is opened. If so, the annular volume can be determined from the gas law, and thus the bulk volume (BV) of the core directly determined within the device.

Initial gas volume in the core under initial conditions is then calculated in SCF and moles.

In this example, the initial volume ($C_o$) calculated in the test is:

0.099758 SCF
0.000263 Moles

Recalculated initial pressure ($P_i$) within the core at the time the chamber was sealed is then determined to be:

70.93157 psia

Figure 4:
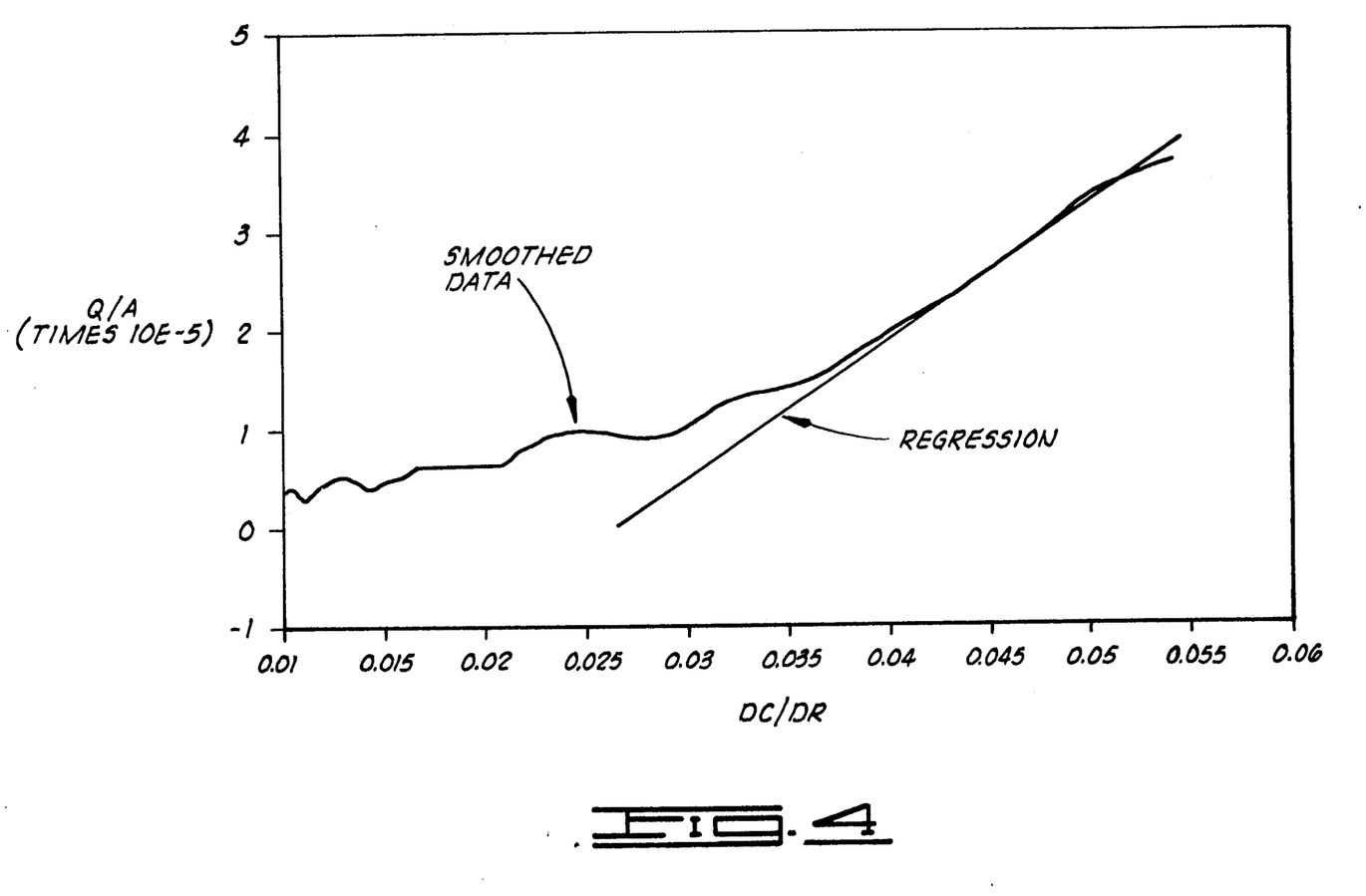
FIG. 4 shows how diffusivity (D) can be obtained for use in calculation of permeability or porosity. D can be obtained by taking the regression fit of the Gas Flow Rate (Q) over the Flow Area Rate (ft$^2$) Surface Area of Core vs. the Gas Concentration Gradient (dc/dr).

To obtain diffusivity, D, the regression fit of the Q/A vs. dc/dr plot (FIG. 4) is calculated, giving the coefficient D described in Eq. 2.

In the example calculation, diffusivity is calculated and given as follows:

D=0.030425

Based on the formula relating diffusivity coefficient to permeability suggested by Ertekin, et. al., the effective gas permeability (K) is obtained as follows:

$$D = \frac{8.0 \times 10^{-2} K_\infty^{0.67}}{P C_g \mu} \quad \text{Equation 3}$$

where:

$K_\infty$ = permeability at $P_\infty$, md
$P$ = pressure, psi
$C_g$ = gas compressibility, $\text{psi}^{-1}$
$\mu$ = gas viscosity, cp By inputting the calculated D into the equation at a given pressure, P, $K_{\infty}$ can be determined.

In the example calculation, an effective gas permeability value, $K_{\infty}$ was determined from the data and input variables as follows:

$K_{\infty}$=0.000187 md
$K_{\infty}$=0.1867 microdarcies

This invention can be performed in "reverse" by a reequilibration with the desired gas at a given pressure and analyzing the pressure build-up curve following gas release into the expansion chamber. Although any "ideal" gas can be used, a gas composition consisting of the measured "natural" gas composition is preferred, assuming the "Z factor" is determined for the particular gas composition.

Summary of Results $C_o$=0.99758 SCF/2.63×$10^{-4}$ Moles
$P_i$=70.93 psia
D=3.0425×$10^{-2}$
$K_{\infty}$=0.187 microdarcies In addition to naturally occurring hydrocarbon reservoirs, this device should have direct application to evaluating hydrocarbon or "gas" storage reservoirs.

Many modifications and variations may be made to the techniques and structures described and illustrated herein without departing from the spirit and scope of the present invention. Accordingly, the described embodiment is illustrative only and is not to be considered as a limitation upon the scope of the present invention.

We claim:

1. A method for determining the permeability and porosity of gas-containing substrate, comprising:
    (a) sealing a sample of a gas containing substrate inside a core analysis vessel comprising a space of known or ascertainable volume as soon as possible after the sample is obtained;
    (b) allowing sufficient time for gas to diffuse out of the sample and into the space of the core analysis vessel;
    (c) measuring the pressure change in the vessel over time, as the pressure in the vessel equilibrates;
    (d) measuring the temperature of the diffused gas in the core analysis vessel over time as the pressure in the vessel equlibrates;
    (e) venting gas from the core analysis vessel to an external pressure which is less than that of the core analysis vessel and measuring gas flow/volume of the vented gas;
    (f) resealing the core analysis vessel and repeating steps (b)–(e) until pressure in sample equilibrates to about the external pressure;
    (g) determining the bulk volume of the sample; and
    (h) calculating the permeability and porosity of the sample based on the vessel volume, sample bulk volume, the measurement of pressure change in the vessel over time, the measurement of flow/volume, and the measurement of temperature over the time in which equilibration(s) occurred.

2. The method of claim 1 wherein the sample substrate is shale, sandstone, or carbonate.

3. The method of claim 1 wherein a sample of a gas depleted substrate is first placed in the core analysis vessel, the core analysis vessel is pressurized to approximate a native pressure by injection of a gas and kept at that pressure for sufficient time for the substrate to internally equilibrate to that pressure, and then upon equilibration, the core analysis vessel is vented to ambient pressure, sealed, and steps (b)–(h) of claim 1 are performed.

4. The method of claim 1 or 6, wherein the sample is placed in a core analysis vessel wherein the ratio of the volume of the core analysis vessel to the bulk volume of the sample is about 1.1 to 1.5.

5. The method of claim 1 wherein the step (a) of sealing said sample into said core analysis vessel is performed within a wellbore penetrating a subterranean formation at an elevated pressure and thereafter the core analysis vessel is removed from the wellbore, the elevated pressure within said vessel is vented to the external pressure and the core analysis vessel is sealed before performance of step (b).

6. A method for determining the permeability and porosity of a sample of subsurface hydrocarbon-bearing matter, comprising:
  (a) down-hole sealing of the sample into a core analysis vessel comprising a space of known or ascertainable volume;
  (b) at about the surface, venting the core analysis vessel to external pressure;
  (c) resealing the core analysis vessel;
  (d) allowing sufficient time for gas to diffuse out of the sample and into the space of the core analysis vessel;
  (e) measuring the pressure change in the vessel over time, as the pressure in the vessel equilibrates;
  (f) measuring the temperature of the diffused gas in the core analysis vessel over time as the pressure in the vessel equilibrates;
  (g) venting gas from the core analysis vessel to an external pressure which is less than the pressure in the vessel and measuring gas flow/volume of the vented gas;
  (h) resealing the core analysis vessel and repeating steps (d)–(g) until pressure in sample equilibrates to about external pressure;
  (i) determining the bulk volume of the sample; and
  (j) calculating permeability and porosity of said sample based on the vessel volume, sample bulk volume, the measurement of pressure change in the vessel over time, the measurement of flow/volume, and the measurement of temperature over the time in which equilibrations occurred.

* * * * *